United States Patent [19]

Tropsha

[11] Patent Number: 5,683,771
[45] Date of Patent: Nov. 4, 1997

[54] BLOOD COLLECTION TUBE ASSEMBLY

[75] Inventor: Yelena G. Tropsha, Chapel Hill, N.C.

[73] Assignee: Becton, Dickinson and Company, Franklin Lakes, N.J.

[21] Appl. No.: 594,068

[22] Filed: Jan. 30, 1996

[51] Int. Cl.[6] .............................. B01L 3/00; B32B 15/16
[52] U.S. Cl. .................. 428/35.9; 428/36.7; 428/36.91; 428/448; 428/701; 428/451; 206/524.2; 220/415; 220/416; 220/457; 128/760; 422/99
[58] Field of Search ................................. 428/35.4, 35.9, 428/36.7, 36.91, 447, 448; 1/451, 701; 206/524.2, 524.3, 524.8; 220/415, 456, 457; 128/760; 422/99

[56] References Cited

U.S. PATENT DOCUMENTS

| | | | |
|---|---|---|---|
| 4,096,315 | 6/1978 | Kubacki | 428/412 |
| 4,140,814 | 2/1979 | Hynecek | 427/39 |
| 4,190,681 | 2/1980 | Hall et al. | 427/45.1 |
| 4,200,681 | 4/1980 | Hall et al. | 428/412 |
| 4,397,897 | 8/1983 | Schülke | 428/35 |
| 4,405,678 | 9/1983 | Downing et al. | 428/215 |
| 4,478,874 | 10/1984 | Hahn | 427/40 |
| 4,490,774 | 12/1984 | Olson et al. | 361/311 |
| 4,647,818 | 3/1987 | Ham | 315/111.21 |
| 4,696,719 | 9/1987 | Bischoff | 202/205 |
| 4,698,256 | 10/1987 | Giglia et al. | 428/216 |
| 4,809,876 | 3/1989 | Tomaswick et al. | 220/458 |
| 4,842,893 | 6/1989 | Yializis et al. | 427/44 |
| 4,846,101 | 7/1989 | Montgomery et al. | 118/723 |
| 4,927,704 | 5/1990 | Reed et al. | 428/221 |
| 4,954,371 | 9/1990 | Yializis | 427/44 |
| 4,992,298 | 2/1991 | Deutchman et al. | 427/38 |
| 5,019,243 | 5/1991 | McEwen et al. | 210/94 |
| 5,032,461 | 7/1991 | Shaw et al. | 428/461 |
| 5,051,308 | 9/1991 | Reed et al. | 428/412 |
| 5,110,633 | 5/1992 | Cassat et al. | 427/430.1 |
| 5,158,750 | 10/1992 | Finicle | 422/102 |
| 5,225,274 | 7/1993 | Ogawa et al. | 428/333 |
| 5,238,746 | 8/1993 | Soga et al. | 428/420 |
| 5,434,008 | 7/1995 | Felts | 428/461 |
| 5,440,446 | 8/1995 | Shaw et al. | 361/301.5 |
| 5,496,295 | 3/1996 | Wilfong et al. | 604/332 |
| 5,545,375 | 8/1996 | Tropsha et al. | 422/102 |

FOREIGN PATENT DOCUMENTS 2 139 647  2/1984  United Kingdom ............ C23C 14/22

OTHER PUBLICATIONS

"Electron Beam Modification of Polymer Film Properties," D.E. Weiss – Radtech International 1992 – Materials Treatment and Modification User Workshop. pp. 687–696.
"The Effect of Plasma–Deposited Silozane Coatings on the Barrier Properties of HDPE," M. Morra, E. Occhiello, and F. Barbassi, *Journal of Applied Polymer Science*, vol. 48, (1993). pp. 1331–1340.

*Primary Examiner*—Charles Nold
*Attorney, Agent, or Firm*—Nanette S. Thomas

[57] ABSTRACT

The present invention is a plastic container coated with a multi-layer barrier coating. The multi-layer barrier coating is useful for providing an effective barrier against gas permeability in containers and for extending shelf-life of containers, especially plastic evacuated blood collection devices.

23 Claims, 6 Drawing Sheets

BLOOD COLLECTION TUBE ASSEMBLY

BACKGROUND OF THE INVENTION

1. Field of the Invention

This invention relates to a multi-layer barrier coating for providing an effective barrier against gas and water permeability for containers, especially plastic blood collection tubes.

2. Description of the Related Art

With the increased emphasis on the use of plastic medical products, a special need exists for improving the barrier properties of articles made of polymers.

Such medical products that would derive a considerable benefit from improving their barrier properties include, but are not limited to, collection tubes and particularly those used for blood collection.

Blood collection tubes require certain performance standards to be acceptable for use in medical applications. Such performance standards include the ability to maintain greater than about 90% original draw volume over a one year period, to be radiation sterilizable and to be non-interfering in tests and analysis.

Therefore, a need exists to improve the barrier properties of articles made of polymers and in particular plastic evacuated blood collection tubes wherein certain performance standards would be met and the article would be effective and usable in medical applications.

SUMMARY OF THE INVENTION

The present invention is a plastic composite container with a multi-layer barrier coating comprising at least two barrier materials disposed over the outer or inner surface of the previously formed composite container. Desirably, the barrier materials comprise a first layer of a polymeric material applied to the outer surface of the previously formed composite container, a second layer of an inorganic material applied over the first layer and a third layer of organic material applied over the second layer.

The first layer, a primer coating, is preferably a highly cross linked acrylate polymer. The coating may be formed either on an interior surface portion, on an exterior surface portion, or both of the container.

The second layer of the barrier coating may preferably be a silicon oxide based composition, such as $SiO_x$ wherein x is from 1.0 to about 2.5; or an aluminium oxide based composition. Most preferably, the second layer is a silicon oxide based composition applied over the first layer.

The third layer of the barrier coating preferably an organic barrier composition, such as poly (vinylidene chloride) (PVDC), is most preferably applied over the second layer.

Preferably, the primer coating is a blend of monoacrylate (i.e., isobornyl acrylate) and diacrylate monomers (i.e., an epoxy diacrylate or a urethane diacrylate) as described in U.S. Pat. Nos. 4,490,774, 4,696,719, 4,647,818, 4,842,893, 4,954,371 and 5,032,461, the disclosures of which are herein incorporated by reference. The primer coating is cured by an electron beam or by a source of ultraviolet radiation.

Desirably, the first layer is formed of a substantially cross linked component selected from the group consisting of polyacrylates and mixtures of polyacrylates and monacrylates having an average molecular weight of between 150 and 1,000 and a vapor pressure in the range of $1 \times 10^{-6}$ to $1 \times 10^{-1}$ Torr at standard temperature and pressure. Most preferably, the material is a diacrylate.

Preferably, the thickness of the acrylate primer coating is about 0.1 to about 10 microns and most preferably from about 0.1 to about 5 microns.

A desirable second layer which is disposed over the first layer preferably comprises a silicon oxide based composition, such as $SiO_x$. Such a film desirably is derived from volatile organosilicon compounds.

The silicon oxide based composition provides a dense, vapor-impervious coating over the primer organic coating. Preferably, the thickness of the silicon oxide based layer is about 100 to about 2,000 Angstroms (Å) and most preferably from about 500 to about 1,000 Å. A coating above 5,000 Å may crack and therefore be ineffective as a barrier.

A desirable third layer which is disposed over the second layer preferably comprises vinylidene chloride - methyl methacrylate - methacrylate acrylic acid polymer (PVDC), thermosetting epoxy coatings, parylene polymers or polyesters.

Preferably, the thickness of the PVDC layer is about 2 to about 15 microns and most preferably from about 3 to about 5 microns.

The process for applying the primer coating to a container is preferably carried out in a vacuum chamber wherein a curable monomer component is metered to a heated vaporizer system where the material is atomized, vaporized and condensed on the surface of the container. Following deposit of the monomer onto the surface of the container, it is cured by suitable means such as electron beam curing. The deposition and curing steps may be repeated until the desired number of layers has been achieved.

A method for depositing a silicon oxide based film is as follows: (a) pretreating the first layer on the container with a first plasma coating of oxygen; (b) controllably flowing a gas stream including an organosilicon compound into a plasma; and (c) depositing a silicon oxide onto the first layer while maintaining a pressure of less than about 500 microns $H_g$ during the depositing.

Although the pretreatment step is optional, it is believed that the pretreatment step provides for improved adherence qualities between the second layer and the primer coating.

The organosilicon compound is preferably combined with oxygen and optionally helium or another inert gas such as argon or nitrogen and at least a portion of the plasma is preferably magnetically confined adjacent to the surface of the first layer during the depositing, most preferably by an unbalanced magnetron.

The PVDC layer is applied over the second layer by dipping or spraying techniques.

Most preferably, the method for depositing a barrier coating on a substrate, such as a plastic collection tube comprises the following steps:

(a) selecting a curable component comprising: i) polyfunctional acrylates, or ii) mixtures of monoacrylates and polyfunctional acrylates;

(b) flash vaporizing said component into said chamber;

(c) condensing a first layer of a film of vaporized component onto the outer surface of said container;

(d) curing said film;

(e) vaporizing an organosilicon component and admixing the volatilized organosilicon component with an oxidizer component and optionally an inert gas component to form a gas steam exterior to the chamber;

(f) establishing a glow discharge plasma in the chamber from one or more of the gas stream components;

(g) controllably flowing the gas stream into the plasma while confining at least a portion of the plasma therein; and (h) depositing a second layer of silicon oxide adjacent said first layer; and (i) dipping a third layer of PVDC over said second layer.

Optionally, the container and/or the first layer may be flame-treated or plasma oxygen treated or corona discharge treated prior to applying the multi-layer coatings.

Plastic tubes coated with the multi-layer barrier coating, comprising the primer coating, and an oxide layer and an overcoating layer are able to maintain substantially far better vacuum retention, draw volume and thermomechanical integrity retention than previous tubes comprised of polymer compositions and blends thereof without a coating of barrier materials or of tubes comprising only an oxide coating. In addition, the tube's resistance to impact is much better than that of glass. Most notably is the clarity of the multi-layer coating and its durability to substantially withstand resistance to impact and abrasion.

Most preferably, the container of the present invention is a blood collection device. The blood collection device can be either an evacuated blood collection tube or a non-evacuated blood collection tube. The blood collection tube is desirably made of polyethylene terephthalate, polypropylene, polyethylene napthalate or copolymers thereof.

Printing may be placed on the multi-layer barrier coating applied to the container of interest. For example, a product identification, bar code, brand name, company logo, lot number, expiration date and other data and information may all be included on the barrier coating. Moreover, a matte finish or a corona discharged surface may be developed on the barrier coating so as to make the surface appropriate for writing additional information on the label. Furthermore, a pressure sensitive adhesive label may be placed over the barrier coating so as to accommodate various hospital overlabels, for example.

Preferably, the multi-layer barrier coating of the present invention provides a transparent or colorless appearance and may have printed matter applied thereon.

A further advantage is that the method of the present invention provides a reduction in the gas permeability of three-dimensional objects that has not been achieved with conventional deposition method typically used with thin films.

It has been found in the present invention that the organic material, acrylate provides a good platform for the growth of the dense $SiO_x$ barrier material.

It has been found that a highly cross linked layer of acrylate improves the adhesion between a plastic surface and $SiO_x$ and overall improves the thermomechanical stability of the coated system. In addition, acrylate primer coating has a role of a planarization (leveling) layer, covering the particles and imperfections on the surface of a polymer and reducing the defect density, in the deposited inorganic coatings. The good bonding properties of the acrylate are also due to the fact that acrylate is polar and the polarity provides means for good bond formation between the $SiO_x$ and the acrylate. In addition, it has been found that a good bond formation is made between plastic tubes made of polypropylene and acrylate. Thus, the present invention provides the means of substantially improving the barrier properties of polypropylene tubes. The adhesion properties of both the acrylate coating and the oxide coating can be further substantially improved by surface pretreatment methods such as flame or oxygen plasma. Therefore, a significant reduction in permeability of the article is due to the substantially improved $SiO_x$ surface coverage that is obtained by the use of a primer coating of acrylate on the plastic article surface.

The layer of PVDC improves the layer of $SiO_x$ because it plugs the defects and/or irregularities in the $SiO_x$ layer. Furthermore, the PVDC layer improves the abrasion resistance of the $SiO_x$ layer.

A plastic blood collection tube coated with the multi-layer barrier coating of the present invention will not interfere with testing and analysis that is typically performed on blood in a tube. Such tests include but are not limited to, routine chemical analysis, biological inertness, hematology, blood chemistry, blood typing, toxicology analysis or therapeutic drug monitoring and other clinical tests involving body fluids. Furthermore, a plastic blood collection tube coated with the barrier coating is capable of being subjected to automated machinery such as centrifuges and may be exposed to certain levels of radiation in the sterilization process with substantially no change in optical or mechanical and functional properties.

DETAILED DESCRIPTION

The present invention may be embodied in other specific forms and is not limited to any specific embodiment described in detail which is merely exemplary. Various other modifications will be apparent to and readily made by those skilled in the art without departing from the scope and spirit of the invention. The scope of the invention will be measured by the appended claims and their equivalents.

Figure 1:
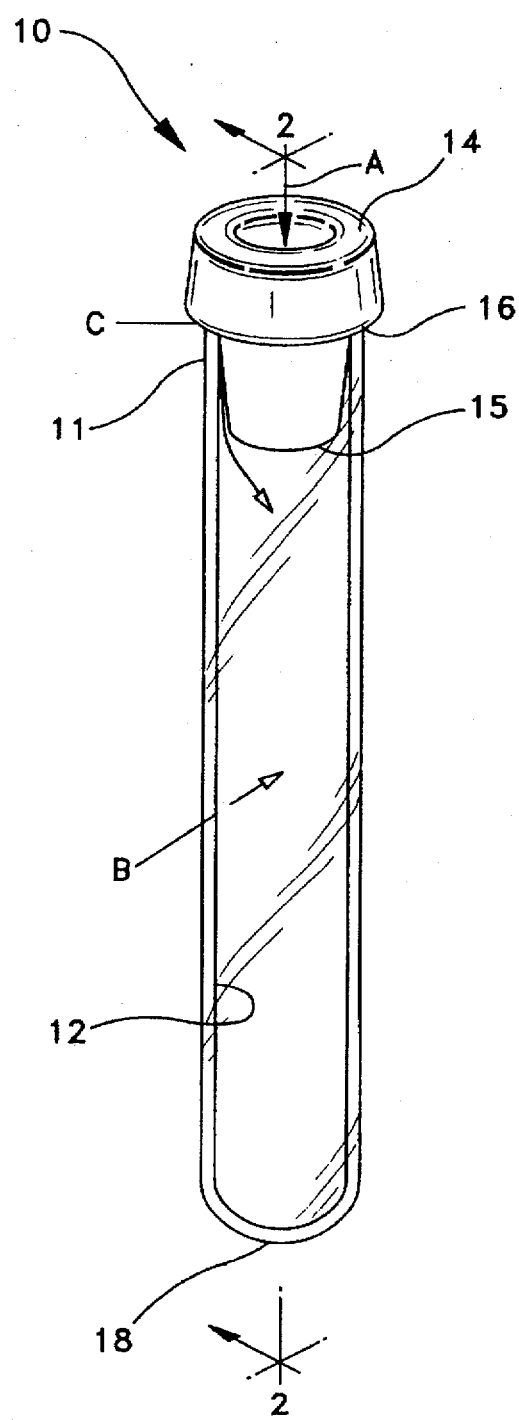
FIG. 1 is a perspective view of a typical blood collection tube with a stopper.
Figure 2:
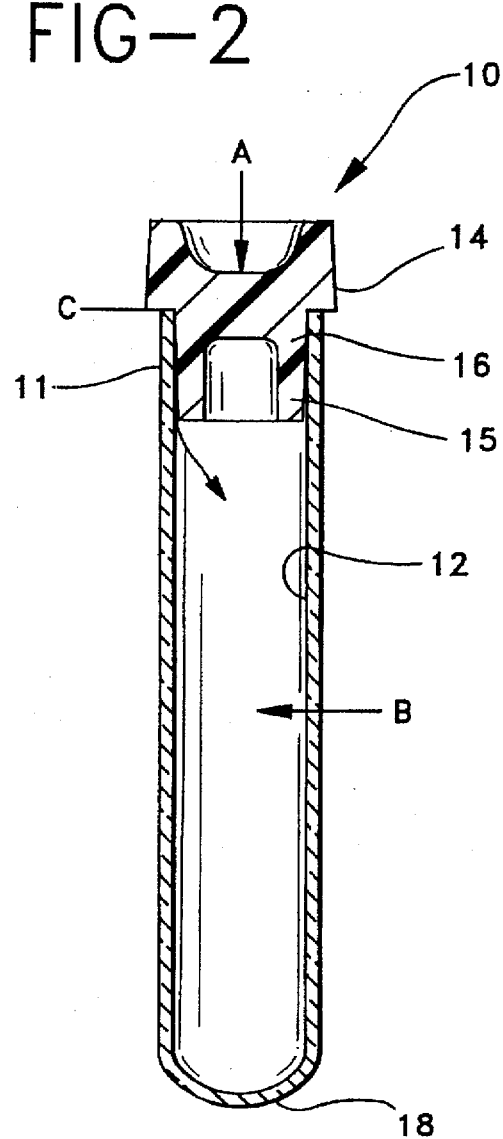
FIG. 2 is a longitudinal sectional view of the tube of FIG. 1 taken along line 2—2.

Referring to the drawings in which like reference characters refer to like parts throughout the several views thereof, FIGS. 1 and 2 show a typical blood collection tube 10, having a sidewall 11 extending from an open end 16 to a closed end 18 and a stopper 14 which includes a lower annular portion or skirt 15 which extends into and presses against the inner surface 12 of the sidewall for maintaining stopper 14 in place.

FIG. 2 schematically illustrates that there are three mechanisms for a change in vacuum in a blood collection tube: (A) gas permeation through the stopper material; (B) gas permeation through the tube and (C) leak at the stopper tube interface. Therefore, when there is substantially no gas permeation and no leak, there is good vacuum retention and good draw volume retention.

Figure 3:
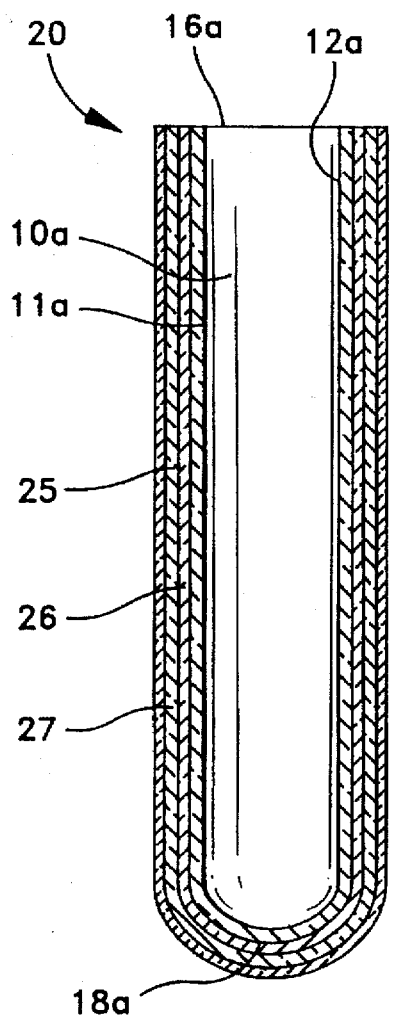
FIG. 3 is a longitudinal sectional view of a tube-shaped container similar to the tube of FIG. 1 without a stopper, comprising a multi-layer barrier coating.

FIG. 3 shows the preferred embodiment of the invention, a plastic tube coated with at least two layers of barrier materials. The preferred embodiment includes many components which are substantially identical to the components of FIGS. 1 and 2. Accordingly, similar components performing similar functions will be numbered identically to those components of FIGS. 1 and 2, except that a suffix "a" will be used to identify those components in FIG. 3.

Referring now to FIG. 3, the preferred embodiment of the invention, collection tube assembly 20 comprises a plastic tube 10a, having a sidewall 11a extending from an opened end 16a to a closed end 18a. A barrier coating 25 extends over a substantial portion of the outer surface of the tube with the exception of open end 16a. Barrier coating 25 comprises a first layer 26 of a polymer material such as an acrylate material and a second layer 27 an inorganic material such as a silicon oxide based composition and a third layer 28 of an organic overcoating layer such as PVDC.

Figure 4:
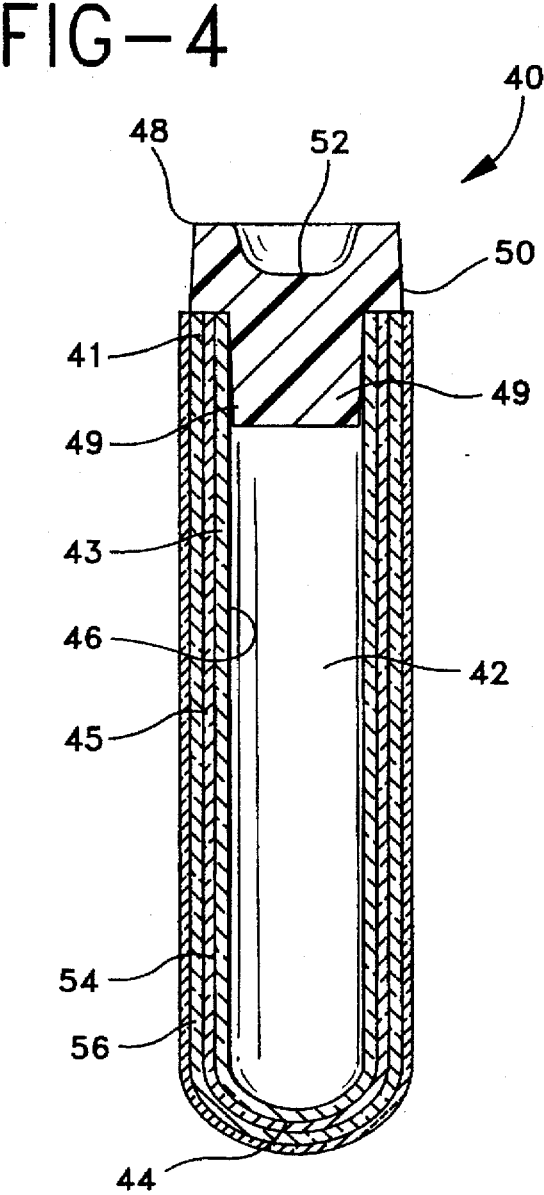
FIG. 4 is a longitudinal sectional view of a tube-shaped container, similar to the tube of FIG. 1 with a stopper, comprising a multi-layer barrier coating.

FIG. 4 illustrates an alternate embodiment of the invention, wherein collection tube assembly 40 comprises stopper 48 in place for closing open end 41 of tube 42. As can be seen, sidewall 43 extends from open end 41 to closed end 44 and stopper 48 includes an annular upper portion 50 which extends over the top edge of tube 42. Stopper 48 includes a lower annular portion or skirt 49 which extends into and presses against the inside inner surface 46 of sidewall 43 for maintaining stopper 48 in place. Also, the stopper has a septum portion 52 for receiving a cannula therethrough.

Thus, the user, once receiving a container such as that shown in FIG. 4 with a sample contained therein, may insert a cannula through septum 52 for receiving part or all of the contents in tube 42 to perform various tests on a sample. Covering a substantial portion of the length of the tube is a multi-layer barrier coating 45. Multi-layer barrier coating 45 covers substantially most of the tube with the exception of open end 41 thereof. Multi-layer barrier coating 45 comprises a first layer 54 of a polymer material such as an acrylate, a second layer 56 of an inorganic material such as a silicon oxide material and a third layer 57 of an organic barrier material such as PVDC. FIG. 4 differs from the embodiment in FIG. 3 in that the tube may be evacuated with the simultaneous placement of stopper 48 therein after the application of layers 54 and 56 over the tube. Alternatively, the multi-layer barrier coating may be applied to the tube after it has been evacuated.

Figure 5:
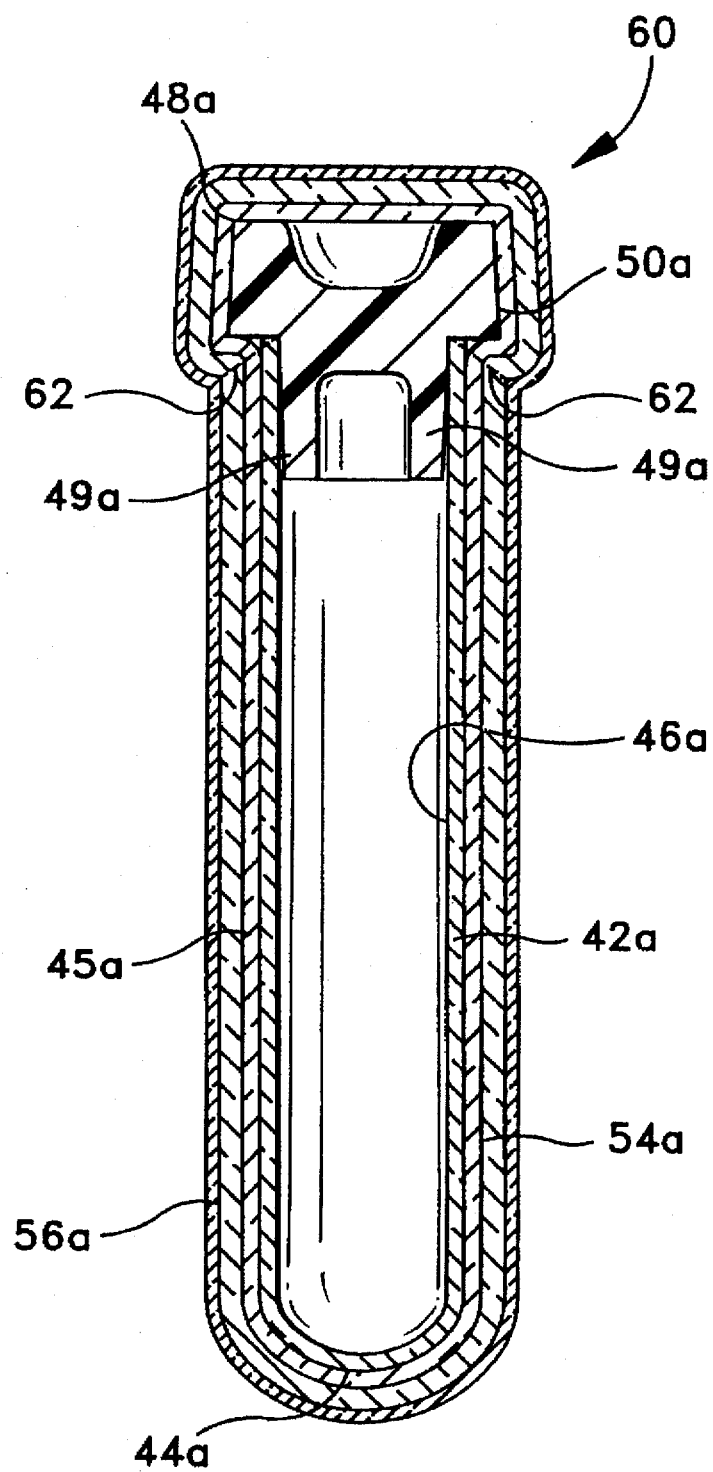
FIG. 5 is a longitudinal sectional view of a further embodiment of the invention illustrating the tube with a stopper similar to FIG. 1 and with the multi-layer barrier coating encompassing both the tube and stopper thereof.

FIG. 5 shows an additional embodiment of the barrier coating and a tube. The alternate embodiment functions in a similar manner to the embodiment illustrated in FIG. 4. Accordingly, similar components performing similar functions will be numbered identically to those components in the embodiment of FIG. 4, except that a suffix "a" will be used to identify those components in FIG. 5.

Referring now to FIG. 5, a further embodiment 60 of the invention wherein multi-layer barrier coating 45a incorporates both upper portion 50a of stopper 48a, as well as the entire outer surface of tube 42a. Multi-layer barrier coating 45a includes serrations 62 at the tube, stopper interface. The serrations are registered so that it can be determined if the sealed container has been tampered with. Such an embodiment may be utilized, for example, for sealing the container with the stopper in place. Once a sample has been placed in the tube, the sample cannot be tampered with by removal of the stopper. Additionally, the serrations may be registered so that it can be determined if the sealed container has been tampered with. Such an arrangement may be appropriate, for example, in drug abuse testing, specimen identification and quality control.

In an alternate embodiment of the invention, multi-layer barrier coating 45 is repeatedly or sequentially applied to the inner and/or outer surface of the tube. Preferably, the coating is applied at least twice.

It will be understood by practitioners-in-the-art, that such tubes may contain reagents in the form of additives or coatings on the inner wall of the tube.

The multi-layer barrier coating forms a substantially clear or translucent barrier. Therefore, the contents of a plastic tube with a multi-layer barrier coating comprising at least two layers of barrier materials are substantially visible to the observer at the same time identifying information may be displayed over the multi-layer barrier coating after it is applied to the plastic tube.

The first layer of the multi-layer barrier coating may be formed on the tube by dip-coating, roll-coating or spraying acrylate monomer or the blend of monomers, followed by UV curing process.

The acrylate polymer material may also be applied to the tube by an evaporation and curing process carried out as described in U.S. Pat. No. 5,032,461, the disclosure of which is herein incorporated by reference.

The acrylate evaporation and curing process involves first atomizing the acrylate monomer into about 50 micron droplets and then flashing them off of a heated surface. This produces an acrylate molecular vapor which has the same chemistry as the starting monomer.

Acrylates are available with almost any chemistry desired. They usually have either one, two or three acrylate groups per molecule. Various mixtures of mono, di and tri acrylates are useful in the present invention. Most preferable are monoacrylates and diacrylates.

Acrylates form one of the most reactive classes of chemicals. They cure rapidly when exposed to UV or electron beam radiation to form a cross-linked structure. This imparts high temperature and abrasion resistant properties in the coating.

The monomer materials utilized are relatively low in molecular weight, between 150 and 1,000 and preferably in the range of 200 to 300 and have vapor pressures between about $1 \times 10^{-6}$ Torr and $1 \times 10^{-1}$ Torr at standard temperature and pressure (i.e., relatively low boiling materials). A vapor pressure of about $1 \times 10^{-2}$ Torr is preferred. Polyfunctional acrylates are especially preferred. The monomers employed have at least two double bonds (i.e., a plurality of olefin groups). The high-vapor-pressure monomers used in the present invention can be vaporized at low temperatures and thus are not degraded (cracked) by the heating process. The absence of unreactive degradation products means that films formed from these low molecular weight, high-vapor-pressure monomers have reduced volatile levels of components. As a result, substantially all of the deposited monomer is reactive and will cure to form an integral film when exposed to a source of radiation. These properties make it possible to provide substantially continuous coating despite the fact that the film is very thin. The cured film exhibits excellent adhesion and are resistant to chemical attack by organic solvents and inorganic salts.

Because of their reactivity, physical properties and the properties of cured films formed from such components, polyfunctional acrylates are particularly useful monomeric materials. The general formula for such polyfunctional acrylates is:

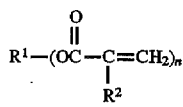

wherein:

$R^1$ is an aliphatic, alicyclic or mixed aliphatic-alicyclic radical;

$R^2$ is a hydrogen, methyl, ethyl, propyl, butyl or pentyl; and n is from 2 to 4.

Such polyfunctional acrylates may also be used in combination with various monacrylates, such as those having the formula:

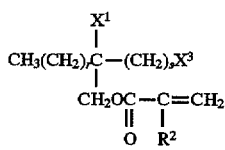

wherein:

$R^2$, is as defined above;

$X^1$ is H, epoxy, 1,6-hexanediol, tripropyleneglycol or urethane; and r, s are 1–18.

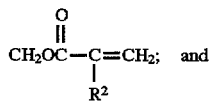

$X^3$ is CN or $COOR^3$ wherein $R^3$ is an alkyl radical containing 1–4 carbon atoms. Most often, $X^3$ is CN or $COOCH_3$.

Diacrylates of the formula below are particularly preferred:

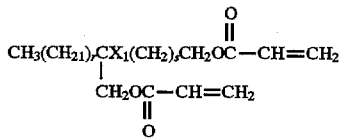

wherein:

$X_1$, r and s are as defined above.

Curing is accomplished by opening the double bonds of the reactant molecules. This can be accomplished by means of an energy source such as apparatus which emits infrared, electrons or ultraviolet radiation.

Figure 6:
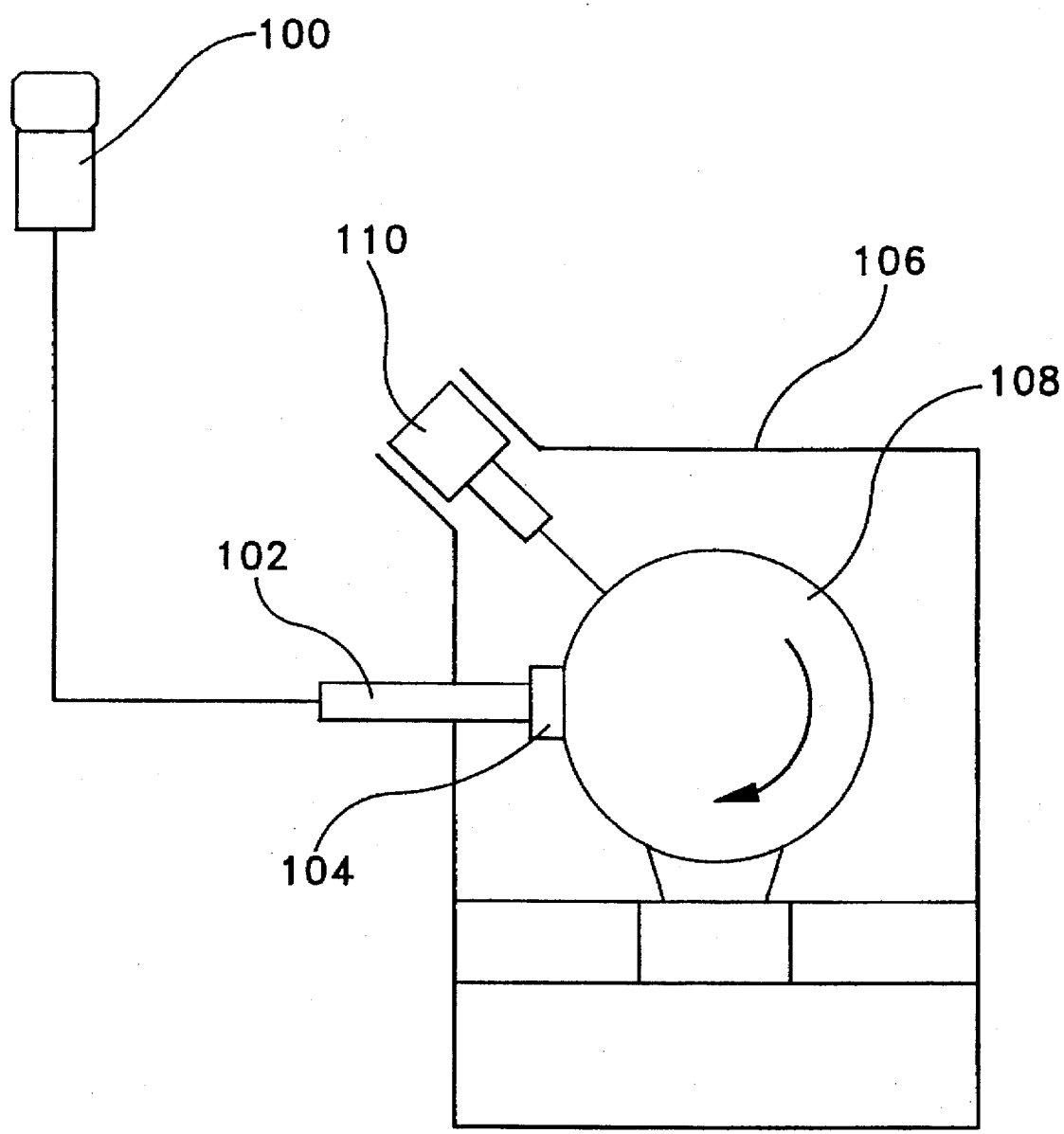
FIG. 6 illustrates an enlarged partially sectioned, diagram of a flash evaporator apparatus.

FIG. 6 illustrates the process for applying an acrylate coating. An acrylate monomer 100 is directed through a dielectric evaporator 102 and then through an ultrasonic atomizer 104 and into a vacuum chamber 106. The monomer droplets are atomized ultrasonically and the droplets vaporized where they condense on the rotating tube or film that is loaded on a drum 108.

The condensed monomer liquid subsequently is radiation cured by means of an electron beam gun 110.

The second layer of the multi-layer barrier coating, an inorganic material, may be formed over the acrylate coating by radio frequency discharge, direct or dual ion beam deposition, sputtering or plasma chemical vapor deposition, as described in U.S. Pat. Nos. 4,698,256, 4,809,876, 4,992,298 and 5,055,318, the disclosures of which are herein incorporated by reference.

For example, a method of depositing an oxide coating is provided by establishing a glow discharge plasma in a previously evacuated chamber. The plasma is derived from one or more of the gas stream components, and preferably is derived from the gas stream itself. The article is positioned in the plasma, preferably adjacent the confined plasma, and the gas stream is controllably flowed into the plasma. A silicon oxide based film is deposited on the substrate to a desired thickness. The thickness of the oxide coating is about 100 Angstroms (Å) to about 10,000 Å. A thickness of less than about 5,000 Å may not provide sufficient barrier and a thickness of greater than about 5,000 Å may crack, thus decreasing the effective barrier. Most preferably, the thickness of the oxide coating is about 1,000 Å to about 3,000 Å.

Another method of depositing an oxide coating is by confining a plasma with magnets. Preferably, the magnetically enhanced method for depositing a silicon oxide based film on a substrate is preferably conducted in a previously evacuated chamber of glow discharge from a gas stream. The gas stream preferably comprises at least two components: a volatilized organosilicon component, an oxidizer component such as oxygen, nitrous oxide, carbon dioxide or air and an optionally inert gas component.

Examples of suitable organosilicon compounds useful for the gas stream in the plasma deposition methods are liquid or gas at about ambient temperature and when volatilized have a boiling point about 0° C. to about 150° C. and include dimethysilane, trimethylsilane, diethylsilane, propylsilane, phenylsilane, hexamethyldisilane, 1,1,2,2-tetramethyldisilane, bis (trimethylsilane)methane, bis (dimethylsilyl) methane, hexamethyldisiloxane, vinyl trimethoxy silane, vinyl triethyoxysilane, ethylmethoxysilane, ethyltrimethoxysilane, divinyltetramethyldisiloxane, hexamethyldsilazane divinyl-hexamethyltrisiloxane, trivinylpentamethyltrisiloxazane, tetraethoxysilane and tetramethoxysilane.

Among the preferred organosilicons are 1,1,3,3-tetramethyldisiloxane, trimethylsilane, hexamethyldisiloxane, vinyltrimethylsilane, methyltrimethoxysilane, vinyltrimethoxysilane and hexamethyldisilazane. These preferred organosilicon compounds have boiling points of 71° C., 55.5° C., 102° C., 123° C. and 127° C. respectively.

The optional inert gas of the gas stream preferably is helium, argon or nitrogen.

The volatilized organosilicon component is preferably admixed with the oxygen component and the inert gas component before being flowed into the chamber. The quantities of these gases being so admixed are controlled by flow controllers so as to adjustably control the flow rate ratio of the gas stream components.

Various optical methods known in the art may be used to determine the thickness of the deposited film while in the deposition chamber, or the film thickness can be determined after the article is removed from the deposition chamber.

The deposition method of the present invention is preferably practiced at relatively high power and quite low pressure. A pressure less than about 500 millitorr (mTorr) should be maintained during the deposition, and preferably the chamber is at a pressure between about 43 to about 490 millitorr during the deposition of film. Low system pressure results in lower deposition rates whereas higher system pressure provides faster deposition rates. When the plastic article to be coated is heat sensitive, a higher system pressure may be used to minimize the amount of heat the substrate is exposed to during deposition because high substrate temperatures are to be avoided for low Tg polymers such as polypropylene and PET (Tg is −10° C. and 60° C. respectively).

The substrate is electrically isolated from the deposition system (except for electrical contact with the plasma) and is at a temperature of less than about 80° C. during the depositing. That is, the substrate is not deliberately heated.

Figure 7:
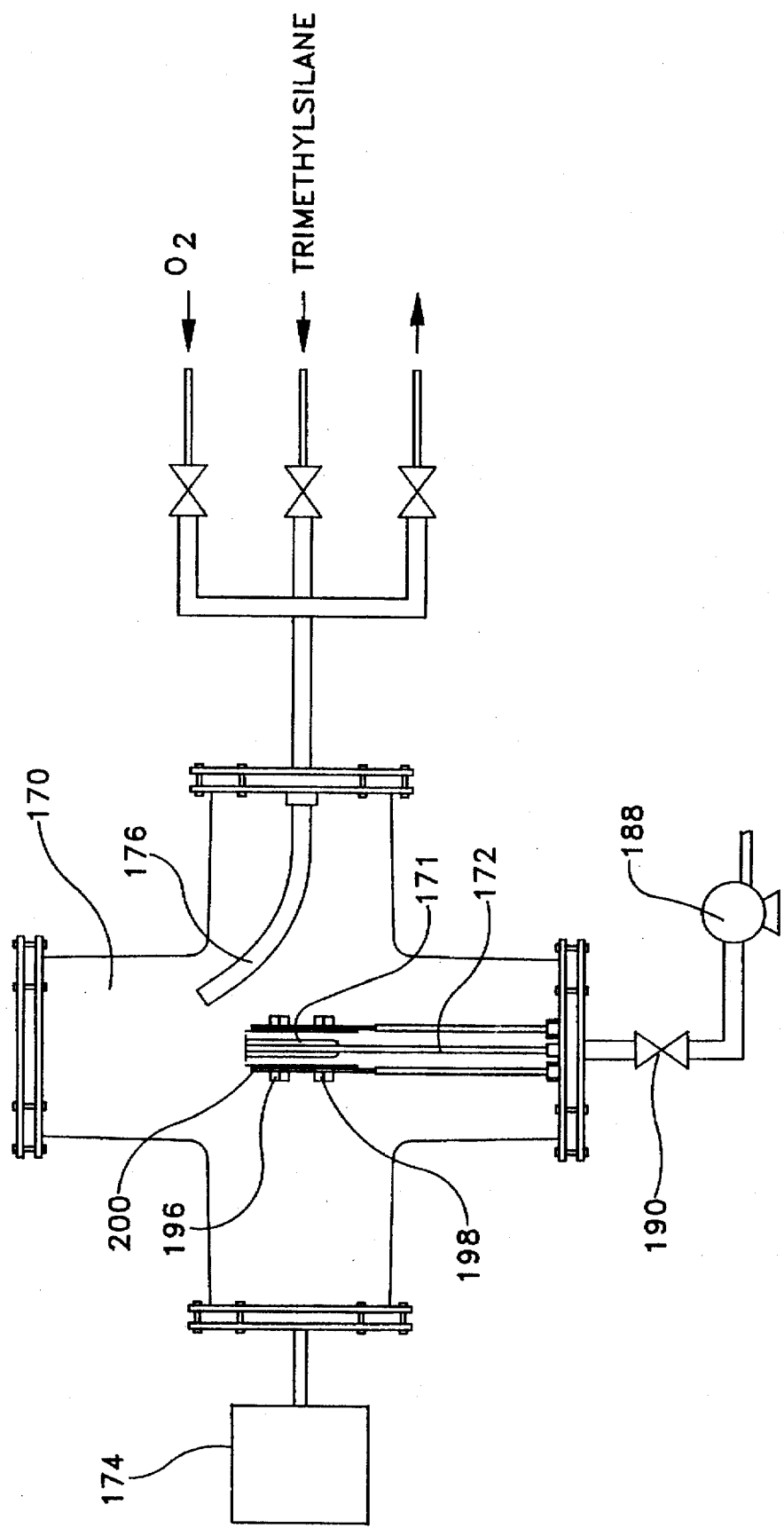
FIG. 7 illustrates a plasma deposition system.

Referring to FIG. 7, the system for depositing a silicon oxide based film comprises an enclosed reaction chamber 170 in which a plasma is formed and in which a substrate or tube 171, is placed for depositing a thin film of material on a sample holder 172. The substrate can be any vacuum compatible material, such as plastic. One or more gases are supplied to the reaction chamber by a gas supply system 173. An electric field is created by a power supply 174.

The reaction chamber can be of an appropriate type to perform any of the plasma-enhanced chemical vapor deposition (PECVD) or plasma polymerization process. Furthermore, the reaction chamber may be modified so that one or more articles may be coated with an oxide layer simultaneously within the chamber.

The pressure of the chamber is controlled by a mechanical pump 188 connected to chamber 170 by a valve 190.

The tube to be coated is first loaded into chamber 170 in sample holder 172. The pressure of the chamber is reduced to about 5 mTorr by mechanical pump 188. The operating pressure of the chamber is about 90 to about 140 mTorr for a PECVD or plasma polymerization process and is achieved by flowing the process gases, oxygen and trimethyl silane, into the chamber through monomer inlet 176.

The thin film is deposited on the outer surface of the tube and has a desired uniform thickness or the deposition process may be interrupted periodically to minimize heating of the substrate and/or electrodes and/or physically remove particulate matter from the articles.

Magnets 196 and 198 are positioned behind electrode 200 to create an appropriate combination of magnetic and electrical fields in the plasma region around the tube.

The system is suitable for low frequency operation. An example frequency is 40 kHz. However, there can be some advantages from operating at a much high frequency, such as in the radio frequency range of several megahertz.

The silicon oxide based film or blends thereof used in accordance with this disclosure, may contain conventional additives and ingredients which do not adversely affect the properties of articles made therefrom.

The third layer of the multi-layer barrier coating may be formed on the second layer by dip-coating, roll-coating or spraying an aqueous emulsion of the polyvinylidene chloride or homo- or co- polymers, followed by air drying.

The third layer may preferably be vinylidene chloride-acrylonitrile-methyl methacrylate-methyl acrylate-acrylic acid copolymers, thermosetting epoxy coatings, parylene polymers, or polyesters.

Preferably, the third layer is a parylene polymer. Parylene is the generic name for members of the polymer series developed by Union Carbide Corporation. The base member of the series, called parylene N, is poly-p-exlylene, a linear, crystalline material:

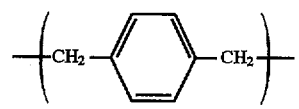

Parylene C, a second member of the parylene series is produced from the same monomer as parylene N and modified by the substitution of a chlorine atom for one of the aromatic hydrogens:

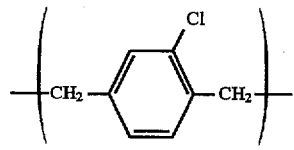

Parylene D, the third member of the parylene series is produced from the same monomer as parylene N and modified by the substitution of the chlorine atom for two of the aromatic hydrogens:

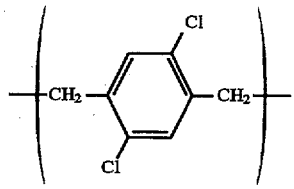

Most preferably, the polymer layer is a vinylidene chloride-methyl methacrylate-methacrylate acrylic acid polymer (PVDC). This polymer is available as DARAN® 8600-C (trademark of W. R. Grace and Co.) sold by GRACE, Organic Chemicals Division, Lexington, Mass.

The third layer of the barrier coating, a polymer material, may be a parylene polymer applied to the second layer by a process similar to vacuum metallizing, as described in U.S. Pat. Nos. 3,342,754 and 3,300,332, the disclosures of which are herein incorporated by reference. Alternatively, the third layer may be vinylidene chloride-acrylonitrile-methyl methacrylate-methyl acrylate-acid acrylic polymer, applied to the second layer by dip-coating, roll-coating or spraying an aqueous emulsion of the polymer, followed by air drying of the coating, as described in U.S. Pat. Nos. 5,093,194 and 4,497,859, the disclosure of which are herein incorporated by reference.

Figure 8:
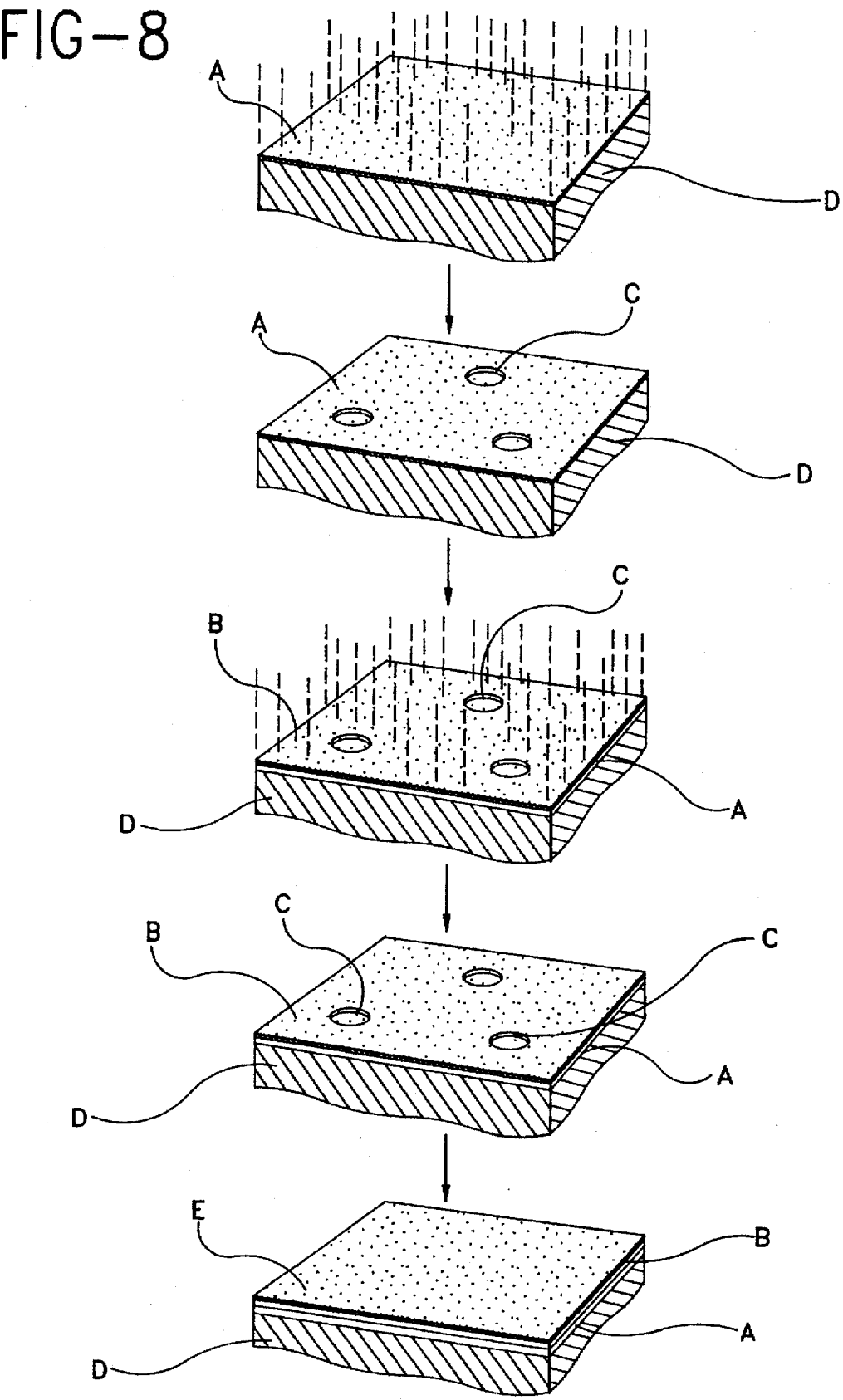
FIG. 8. is a general schematic diagram illustrating the layers being deposited on a substrate.

As shown in FIG. 8, the acrylate coating A and the silicon oxide based coating B may have defects or irregularities C. It is believed that complete coverage of the substrate D cannot be achieved with only the acrylate and silicon oxide based coatings. Therefore, a third coating of PVDC, E is applied over the silicon oxide based coating to produce a substantially complete barrier coating over the substrate surface.

A variety of substrates can be coated with a barrier coating by the process of the present invention. Such substrates include, but are not limited to packaging, containers, bottles, jars, tubes and medical devices.

A plastic blood collection tube coated with the multi-layer barrier coating will not interfere with testing and analysis that is typically performed on blood in a tube. Such tests include but are not limited to, routine chemical analysis, biological inertness, hematology, blood chemistry, blood typing, toxicology analysis or therapeutic drug monitoring and other clinical tests involving body fluids. Furthermore, a plastic blood collection tube coated with the barrier coating is capable of being subjected to automated machinery such as centrifuges and may be exposed to certain levels of radiation in the sterilization process with substantially no change in optical or mechanical and functional properties.

A plastic blood collection tube coated with the multi-layer barrier coating is able to maintain 90% original draw volume over a period of one year. Draw volume retention depends on the existence of a particle vacuum, or reduced pressure, inside the tube. The draw volume changes in direct proportion to the change in vacuum (reduced pressure). Therefore, draw volume retention is dependent on good vacuum retention. A plastic tube coated with a barrier coating substantially prevents gas permeation through the tube material so as to maintain and enhance the vacuum retention and draw volume retention of the tube. Plastic tubes without the multi-layer coating of the present invention may maintain about 90% draw volume for about 3 to 4 months.

If the multi-layer barrier coating is also coated or applied on the inner surface of the plastic blood collection tube, the barrier coating may be hemorepellent and/or have characteristics of a clot activator.

It will be understood that it makes no difference whether the plastic composite container is evacuated or not evacuated in accordance with this invention. The presence of a barrier coating on the outer surface of the container has the effect of maintaining the general integrity of the container holding a sample so that it may be properly disposed of without any contamination to the user. Notable is the clarity of the barrier coating as coated or applied on the container and its abrasion and scratch resistance.

The barrier coating used in accordance with this disclosure, may container conventional additives and ingredients which do not adversely affect the properties of articles made therefrom.

The following examples are not limited to any specific embodiment of the invention, but are only exemplary.

EXAMPLE 1

Method For Coating Plastic Substrates Tubes With Multi-Layer Barrier Coating

An acrylate coating was applied to polypropylene tubes and films (substrates) of various thickness in a chamber wherein Tripropylene Glycol Diacrylate (TPGDA) was fed into the evaporator and was flash vaporized at about 343° C. onto the substrate in the chamber and condensed. The condensed monomer film was then E-beam cured by an electron beam gun.

The substrate coated with the acrylate coating (TPGDA) was then cleaned with a mixture comprising equal parts of a micro detergent and de-ionized (DI) water solution. The substrate was rinsed thoroughly in DI water and allowed to air dry. The cleaned substrate was then stored in a vacuum oven at room temperature until it was to be coated.

The cleaned substrate was then attached to a holder which fits midway between the electrodes in the glass vacuum chamber. The chamber was closed and a mechanical pump was used to achieve a base pressure of 5 mTorr.

The electrode configuration is internally capacitively coupled with permanent magnets on the backside of the titanium electrodes. This special configuration provides the ability to confine the glow between the electrodes because of the increase in collision probability between electrons and reacting gas molecules. The net result of applying a magnetic field is similar to increasing the power applied to the electrodes, but without the disadvantages of higher bombardment energies and increased substrate heating. The use of magnetron discharge allows operation in the low pressure region and a substantial increase in polymer deposition rate.

The monomer which consists of a mixture of trimethylsilane (TMS) and oxygen was introduced through stainless steel tubing near the electrodes. The gases were mixed in the monomer inlet line before introduction into the chamber. Flow rates were manually controlled by stainless steel metering valves. A power supply operating at an audio frequency of 40 kHz was used to supply power to the electrodes. The system parameters used for thin film deposition of plasma polymerized TMS/O$_2$ on the polymer substrate were as follows:

| Surface Pretreatment: | TMS Flow = | 0 sccm |
|---|---|---|
| | Base Pressure = | 5 mTorr |
| | Oxygen Flow = | 10 sccm |
| | System Pressure = | 140 mTorr |
| | Power = | 50 watts |
| | Time = | 2 minutes |
| Oxide Deposition: | TMS Flow = | 0.75–1.0 sccm |
| | Oxygen Flow = | 2.5 = 3.0 sccm |
| | System Pressure = | 90–100 mTorr |
| | Power = | 30 watts |
| | Deposition Time = | 5 minutes |

After the thin film was deposited, the reactor was allowed to cool. The reactor was then opened, and the substrate was removed.

A protective topcoating of a water-based emulsion of PVDC copolymer was applied by dip coating and cured at 65° C. for about 10 minutes to produce a final coating thickness averaging about 6 microns.

EXAMPLE 2

Method For Coating Plastic Substrates With Multi-Layer Barrier Coating

An acrylate coating was applied to polypropylene tubes and films (substrates) in a chamber wherein a 60:40 mixture of isobornyl acrylate: epoxydiacrylate (IBA:EDA) was fed into the evaporator and flash vaporized at about 343° C. onto the substrate in the chamber and condensed. The condensed monomer film was then UV cured by an actinic light source of 365 nm.

The substrate coated with the acrylate coating (IBA:EDA) was then cleaned with a mixture comprising equal parts of a micro detergent and de-ionized (DI) water solution. The substrate was rinsed thoroughly in DI water and allowed to air dry. The cleaned substrate was then stored in a vacuum oven at room temperature until it was to be coated.

The cleaned substrate was then attached to a holder which fits midway between the electrodes in the glass vacuum chamber. The chamber was closed and a mechanical pump was used to achieve a base pressure of 5 mTorr.

The electrode configuration is internally capacitively coupled with permanent magnets on the backside of the titanium electrodes. The special configuration provides the ability to confine the glow between the electrodes because of the increase in collision probability between electrons and reacting gas molecules. The net result of applying a magnetic field is similar to increasing the power applied to the electrodes, but without the disadvantages of higher bombardment energies and increased substrate heating. The use of magnetron discharge allows operation in the low pressure region and a substantial increase in polymer deposition rate.

The monomer which consists of a mixture of trimethylsilane (TMS) and oxygen was introduced through stainless steel tubing near the electrodes. The gases were mixed in the monomer inlet line before introduction into the chamber. Flow rates were manually controlled by stainless steel metering valves. A power supply operating at an audio frequency of 40 kHz was used to supply power to the electrodes. The system parameters used for thin film deposition of plasma polymerized TMS/$O_2$ on the polymer substrate were as follows:

| Surface Pretreatment: | TMS Flow = | 0 sccm |
|---|---|---|
| | Base Pressure = | 5 mTorr |
| | Oxygen Flow = | 10 sccm |
| | System Pressure = | 140 mTorr |
| | Power = | 50 watts |
| | Time = | 2 minutes |
| Oxide Deposition: | TMS Flow = | 0.75–1.0 sccm |
| | Oxygen Flow = | 2.5 = 3.0 sccm |
| | System Pressure = | 90–100 mTorr |
| | Power = | 30 watts |
| | Deposition Time = | 5 minutes |

After the thin film was deposited, the reactor was allowed to cool. The reactor was then opened, and the substrate with a multi-layer barrier coating was removed.

A protective topcoating of a water-based emulsion of PVDC copolymer was applied by dip coating and cured at 65° C. for about 10 minutes to produce a final coating thickness averaging about 6 microns.

EXAMPLE 3

Comparison of Substrates With and Without Multi-Layer Barrier Coatings

All of the substrates prepared in accordance with Examples 1 and 2 above were evaluated for oxygen permeance (OTR) in the oxide coatings as follows.

(i) Oxygen Permeance (OTR):

Film or plaque samples were tested for oxygen permeance (OTR) using a MO CON $O_x$-TRAN 2/20 (sold by Modern Controls, Inc., 7500 Boone Avenue N., Minneapolis, Minn. 55428). A single side of the film sample was exposed to 1 atm of 100% oxygen atmosphere. Oxygen permeating through the sample film was entrained in a nitrogen carrier gas stream on the opposite side of the film, and detected by a coulmetric sensor. An electrical signal was produced in proportion to the amount of oxygen permeating through the sample. Samples were tested at 30° C. and 0% relative humidity (R.H.). Samples were conditioned for 1 to 20 hours prior to determining oxygen permeance. The results are reported in Table 1 in units of cc/m2-atm-day.

Tube samples were tested for oxygen permeance (OTR) using a MOCON $O_x$-TRAN 1,000 (sold by Modern Controls, Inc., 7500 Boone Avenue N., Minneapolis, Minn. 55428). A package adapter was used for mounting the tubes in a manner that allowed the outside of the tube to be immersed in a 100% $O_2$ atmosphere while the inside of tube is flushed with a nitrogen carrier gas. The tubes were then tested at 20° C. and 50% R.H. The tubes were allowed to equilibrate for 2–14 days before a steady state permeability is determined. The results are reported in Table 1 in units of cc/$m^2$-atm-day.

TABLE 1

| Sample | Acrylate Coating | $SiO_x$ Coating | PVDC Coating | Oxygen Transmission Rate (cc/$m^2$-atm-day) 30° C., 0% RH |
|---|---|---|---|---|
| PP film, control | no | no | | 1500 |
| PP plaque, 75 mil | no | yes | | 37 |
| PP plaque, 75 mil | TPGDA | yes | | 3.5 |
| PP plaque, control | no | no | | 65 |
| PP tube, control | no | no | | 70 |
| PP tube | IBA:DA | no | | 70 |
| PP tube | no | yes | | 46–60 |
| PP tube | IBA:DA | yes | | 4.3–6.4 |
| PP tube | IBA:DA | yes | yes | 2.5 |
| PP tube | TPGDA | yes | yes | 5 |

IBA:DA = iso-nornornyl: epoxydiacrylate (60:40), UV cured
TPGAD = tripropylene glycol diacrylate E-beam cured
Oxide Coatings = 1000–3000 Angstroms (as measured by Scanning Electron Microscope)
PP = polypropylene
plaque = 75 mil thickness
film = 2 mil thickness
tubes = nominal wall thickness of 40 mil

What is claimed is:

1. A sample assembly comprising:
    a plastic container having an open end, a closed end, an inner surface and an outer surface; and
    a multi-layer barrier coating associated over the outer surface of said container and extending over a major portion of said outer surface of said container, said coating having a first layer comprising an acrylate primer coating material, a second layer on said first layer comprising a metal oxide and a third layer on said second layer comprising an organic material.

2. The assembly of claim 1, further comprising a closure in said open end of said container whereby a container and closure interface is formed.

3. The assembly of claim 2, wherein said plastic container is a tube and said closure is an elastomeric stopper.

4. The assembly of claim 1, wherein said barrier coating extends substantially from said open end of said container to and over said closed end of said container.

5. The assembly of claim 3, wherein said barrier coating extends from a portion of said elastomer stopper to a point adjacent said closed end of said container.

6. The assembly of claim 2, wherein said tube is evacuated.

7. The assembly of claim 5, wherein said multi-layer barrier coating includes registered tamper serrations adjacent to said container and said closure interface.

8. The assembly of claim 1, wherein said first layer is a polymerized blend of mono- and di-acrylates.

9. The assembly of claim 1, wherein said second layer is aluminum oxide or silicon oxide based composition.

10. The assembly of claim 9, wherein said second layer comprises silicon oxide.

11. The assembly of claim 9, wherein said second layer is deposited by radio-frequency discharge, direct ion beam deposition, dual ion beam deposition, sputtering, plasma chemical vapor deposition or magnetically enhanced plasma systems.

12. The assembly of claim 1, wherein said third layer is thermosetting epoxy, parylene polymer, homo-polymers, co-polymers or polyesters.

13. The assembly of claim 1, wherein said first layer comprises polymerized acrylate and said second layer comprises silicon oxide and said third layer comprises polyvinylidene chloride.

14. The assembly of claim 1, further comprising a multi-layer barrier coating over the inner surface of said container, having a first layer including an acrylate primer coating material, a second layer on said first layer of a metal oxide and a third layer of an organic material.

15. A multi-layer barrier coating comprising:

a first layer comprising an acrylate material;

a second layer on said first layer comprising a metal oxide;

and a third layer on said second layer comprising an organic material.

16. The coating of claim 15, wherein said second layer is aluminum oxide or silicon oxide.

17. The coating of claim 15, wherein said third layer is polyvinylidene chloride.

18. The assembly of claim 1, wherein said first layer is deposited on said outer surface of said container in a previously evacuated chamber comprising the following steps:

(a) selecting a curable component comprising: i) polyfunctional acrylates, or ii) mixtures of monoacrylates and polyfunctional acrylates;

(b) flash vaporizing said component into said chamber;

(c) condensing a film of vaporized component onto the outer surface of said container; and (d) curing said film.

19. The assembly of claim 18, wherein said second layer is deposited in said previously evacuated chamber onto said first layer by the following steps:

(a) vaporizing an organosilicon component and admixing the volatilized organosilicon component with an oxidizer component and optionally an inert gas component to form a gas steam exterior to the chamber;

(b) establishing a glow discharge plasma in the chamber from one or more of the gas stream components;

(c) controllably flowing the gas stream into the plasma while confining at least a portion of the plasma therein; and (d) depositing a layer of silicon oxide adjacent said first layer.

20. The assembly of claim 19, wherein said oxidizer component is oxygen nitrous oxide, carbon dioxide, air, or an inert compound.

21. The assembly of claim 19, wherein the plastic substrate is electrically isolated from the chamber except for contact with the confined plasma.

22. The assembly of claim 14, wherein said third layer is a parylene polymer.

23. The assembly of claim 14, wherein said parylene polymer is parylene N, parylene C or parylene D.

* * * * *